United States Patent
Lo et al.

(10) Patent No.: US 12,056,258 B2
(45) Date of Patent: Aug. 6, 2024

(54) ANONYMIZATION OF HETEROGENOUS CLINICAL REPORTS

(71) Applicant: Siemens Healthineers AG, Forchheim (DE)

(72) Inventors: Ren-Yi Lo, Plainsboro, NJ (US); Poikavila Ullaskrishnan, Lebanon, NH (US)

(73) Assignee: Siemens Healthineers AG, Forchheim (DE)

( * ) Notice: Subject to any disclaimer, the term of this patent is extended or adjusted under 35 U.S.C. 154(b) by 785 days.

(21) Appl. No.: 16/868,377

(22) Filed: May 6, 2020

(65) Prior Publication Data
US 2020/0387635 A1  Dec. 10, 2020

(30) Foreign Application Priority Data
Jun. 5, 2019 (EP) .................... 19178526

(51) Int. Cl.
*G16H 15/00* (2018.01)
*G06F 16/11* (2019.01)
*G06F 21/62* (2013.01)
*G06N 5/04* (2023.01)
*G06N 20/00* (2019.01)
(Continued)

(52) U.S. Cl.
CPC ........ *G06F 21/6254* (2013.01); *G06F 16/116* (2019.01); *G06N 5/04* (2013.01); *G06N 20/00* (2019.01); *G16H 10/60* (2018.01); *G16H 15/00* (2018.01); *G16H 50/20* (2018.01); *G16H 50/70* (2018.01)

(58) Field of Classification Search
CPC ..... G06F 21/6254; G06F 16/116; G06N 5/04; G06N 20/00; G16H 10/60; G16H 15/00; G16H 50/20; G16H 50/70; G16H 10/20
See application file for complete search history.

(56) References Cited

U.S. PATENT DOCUMENTS

2017/0199963 A1 * 7/2017 Kondadadi ............ G16H 15/00
2018/0107791 A1   4/2018 Guo et al.
(Continued)

FOREIGN PATENT DOCUMENTS

EP  3096258 A1  11/2016
EP  3188058 A1   7/2017

OTHER PUBLICATIONS

Aberdeen, John, et al. "The MITRE Identification Scrubber Toolkit: design, training, and assessment." International journal of medical informatics 79.12 (2010): 849-859.
(Continued)

*Primary Examiner* — Maroun P Kanaan

(57) ABSTRACT

For anonymizing or other keyword identification medical patient data, a conditional random field sequence classifier is used for the NER model for NLP, providing a technical solution to help the computer perform better at identifying PHI from context and reduce manual anonymization efforts of medical reports. One tool or executable integrates report format conversion, annotation, training, and application. These operations may be selected, or the tool configured for anonymization or keyword identification. Different files from each stage may be exported or used by others operating on other computers, allowing collaboration or sequential burden sharing for anonymization.

18 Claims, 7 Drawing Sheets

(51) Int. Cl.
   *G16H 10/60* (2018.01)
   *G16H 50/20* (2018.01)
   *G16H 50/70* (2018.01)

(56) References Cited

U.S. PATENT DOCUMENTS

2018/0129900 A1\* 5/2018 Kiraly ................ G06N 3/08
2020/0160970 A1\* 5/2020 Lyman ............... A61B 5/7264

OTHER PUBLICATIONS

Brief, OCR Privacy. "Summary of the HIPAA Privacy Rule." Washington, DC, United States Department of Health and Human Services (2005).
Esuli, Andrea, et al. "Evaluating information extraction." International Conference of the Cross-Language Evaluation Forum for European Languages. Springer, Berlin, Heidelberg, 2010.
Federal Register (2009) / vol. 74, No. 209 / Friday, Oct. 30, 2009 / Rules and Regulations, 56123-56131.
Finkel, Jenny Rose, et al. "Incorporating non-local information into information extraction systems by gibbs sampling." Proceedings of the 43rd annual meeting on association for computational linguistics. Association for Computational Linguistics, 2005.
MIST. "The MITRE Identification Scrubber Toolkit—How does it work?" http://mist-deid.sourceforge.net/ accessed May 13, 2019.
National Institute of Biomedical Imaging and Bioengineering (NIBIB), under grant R01 EB001659. "De-Identification: Software and Test Data" https://alpha.physionet.org accessed May 13, 2019.
Neamatullah, Ishna, et al. "Automated de-identification of free-text medical records." BMC medical informatics and decision making 8.1 (2008): 32.
Pierorazio, Phillip M., et al. "Prognostic G leason grade grouping: data based on the modified G leason scoring system." BJU international 111.5 (2013): 753-760.
Regulation, General Data Protection. "Regulation (EU) 2016/679 of the European Parliament and of the Council of Apr. 27, 2016 on the protection of natural persons with regard to the processing of personal data and on the free movement of such data, and repealing Directive 95/46." Official Journal of the European Union (OJ) 59. (2016).
Uzuner, Özlem, Yuan Luo, and Peter Szolovits. "Evaluating the state-of-the-art in automatic de-identification." Journal of the American Medical Informatics Association 14.5 (2007): 550-563.
Exended European Search Report (EESR) mailed Dec. 11, 2019 in corresponding European Patent Application No. 19178526.0-1126.
Anonymous; "Supervised learning"; Wikipedia, the free encyclopedia; Sep. 30, 2011; XP055648796; Retrieved from the Internet: URL:https://web.archive.org/web/20110930200825/http://en.wikipedia.org/wiki/Supervisedlearning.
Barigou Fatiha et al; "MedIX: A named entity extraction tool from patient clinical reports"; Communications, Computing and Control Application (CCCA); 2011 International Conference on IEEE; Mar. 3, 2011; pp. 1-6; DOI: 10.1109/CCCA.2011.6031494; ISBN: 978-1-4244-9795-9.
Fatiha Barigou et al: "Using a Cellular Automaton to Extract Medical Information from Clinical Reports"; Journal of Information Processing Systems;vol. 8; No. 1; Mar. 31, 2012 (Mar. 31, 2012); pp. 67-84.

\* cited by examiner

```
XYZ Hospital
DEF Street Phone: 333-333-3333 Fax: 888-888-888              50

Patient: ANNE, MARY
Gender: F
Address: ABC Street, New York, 56789
MRN : M000012345
Referring Physician: ANDREW, WILLIAM
CT OF THE CTA CHEST HISTORY: Rule out pulmonary embolism
COMPARISON: None Exam Date: DOB: FAX:

01/07/2018  09/24/1920  888-888-888

TECHNIQUE: Routine noncontrast scan of the Brain, neck, chest, abdomen,
and pelvis was performed using a 64 slice CT scanner.
FINDINGS: Frontal scout views of the head are unremarkable. The cervical vertebral bodies appear in
alignment body heights and internal densities are well preserved.
IMPRESSION: Disc degenerative change in the cervical spine at the C5-C6 level with
associated joint arthrosis producing no significant narrowing of the neural foramina. Groundglass
opacities are seen bilaterally. The accession number of the patient is ACCN018888. FRoutine
screening studies such as colonoscopy, physical examination, and blood tests should be performed at
the direction of the patient's personal physician. Dr. JOHN was notified at 1:13 AM 1/7/2018. Thank
you for your kind referral of this patient.
```

FIG. 5A

```
XYZ Hospital
DEF Street Phone: 333-333-3333 Fax: 888-888-888              52

Patient: MARY, JANE
Gender: M
Address: EFG Street, London, 13579
MRN : M000056789
Referring Physician: SMITH, ADAM
CT OF THE CTA CHEST CTA OF CHEST (CT-PULMONARY ANGIOGRAM) History: Hypotension.
Comparison: No prior CTA of the chest available Exam Date: DOB: FAX:

01/27/2018  05/29/1943  888-888-888

Technique: Sequential images were acquired from the thoracic inlet to the upper abdomen without
intravenouscontrast material. A tiny nonspecific 3 mm nodular density is noted in the lateral
aspect of the right lower lobe. There appears to be some atelectasis of the right lower lobe as
well as herniation of the liver and solid abdominal organs of the right upper quadrant into this
region. The accession number of the patient is ACCN02999.
Impression: No definite evidence of pulmonary embolism is identified.
Electronically Signed by: DOE, JOHN, MD, FELLOWSHIP TRAINED MSK & BODY SUBSPECIALIST on 12/26/2017
9:09:57 PM.
```

FIG. 5B

Removables Configuration File
60
* XYZ Hospital
* DEF Street Phone: 333-333-3333 Fax: 888-888-888
* 888-888-888
* *ACCNO*18888

Headerfields Configuration File
* Address:
* MRN:

```
**REMOVED
**REMOVED                                                              100

Patient: **PERSON
Gender: F
Address: **HEADERFIELD
MRN : **HEADERFIELD
Referring Physician: **PERSON
CT OF THE CTA CHEST HISTORY: Rule out pulmonary embolism
COMPARISON: None Exam Date: DOB: FAX:

DATE DATE **REMOVED

TECHNIQUE: Routine noncontrast scan of the Brain, neck, chest, abdomen,
and pelvis was performed using a 64 slice CT scanner.
FINDINGS: Frontal scout views of the head are unremarkable. The cervical vertebral bodies appear in
alignment body heights and internal densities are well preserved.
IMPRESSION: Disc degenerative change in the cervical spine at the C5-C6 level with
associated joint arthrosis producing no significant narrowing of the neural foramina. Groundglass
opacities are seen bilaterally. The accession number of the patient is **REMOVED. FRoutine
screening studies such as colonoscopy, physical examination, and blood tests should be performed at
the direction of the patient's personal physician. **PERSON was notified at **TIME **DATE. Thank
you for your kind referral of this patient.
```

FIG. 10A

```
**REMOVED
**REMOVED                                                              102

Patient: **PERSON
Gender: M
Address: **HEADERFIELD
MRN : **HEADERFIELD
Referring Physician: **PERSON
CT OF THE CTA CHEST CTA OF CHEST (CT-PULMONARY ANGIOGRAM) History: Hypotension.
Comparison: No prior CTA of the chest available Exam Date: DOB: FAX:

DATE DATE **REMOVED

Technique: Sequential images were acquired from the thoracic inlet to the upper abdomen without
intravenouscontrast material. A tiny nonspecific 3 mm nodular density is noted in the lateral
aspect of the right lower lobe. There appears to be some atelectasis of the right lower lobe as
well as herniation of the liver and solid abdominal organs of the right upper quadrant into this
region. The accession number of the patient is **REMOVED.
Impression: No definite evidence of pulmonary embolism is identified.
Electronically Signed by: **PERSON, FELLOWSHIP TRAINED MSK & BODY SUBSPECIALIST on **DATE **TIME.
```

FIG. 10B

ANONYMIZATION OF HETEROGENOUS CLINICAL REPORTS

RELATED CASE

This application claims the benefit of EP 19178526.0, filed on Jun. 5, 2019, which is hereby incorporated by reference in its entirety.

BACKGROUND

The present embodiments relate to anonym ization of medical information. Any dataset used within the framework of healthcare research in the USA must be anonymized as per the Health Insurance Portability and Accountability Act (HIPAA) and the Health Information Technology for Economic and Clinical Health Act (HITECH). Similarly, the dataset must satisfy the General Data Protection Regulation (GDPR) regulations of patient de-identification when used within European Union (EU) or when collected from citizens of the EU. Other countries have their own data privacy regulations. The aim of these regulations is to make datasets free of information that can uniquely identify a patient (i.e., Protected Health Information (PHI)) when PHI is not necessary in the use of the data. Some common attributes that are considered PHI are first name and last name, birthday, street address, and social security number, but other attributes, such as institution name where the patient was treated, may be considered PHI in one country but not in another country. To fully anonymize the data (e.g., make PHI-free) depends on the data source as well as what rules and regulations govern that data.

The most popular format for storing, transmitting and viewing medical images is DICOM. A large suite of solutions is available to anonym ize DICOM images and DICOM structured reports. However, accompanying medical reports or additional clinical information that is not in the DICOM format is equally relevant and important in research. Despite relevance and prevalence of medical reports, there has been no effective solution to anonymize the medical reports. Clinical reports come in different formats, such as pdfs, docs, excel, and text files, depending on the hospital, department or even type of examination. Within each hospital, each radiologist might have a different way of entering his or her findings and patient information. Any effective solution must be compatible enough to work with these different document formats and structures.

In one approach to avoid manual anonymization, natural language processing (NLP) is used to create name-entity recognition (NER) models, which identify PHI. In the training phase for NLP, a list of word-entity pairs is given. For example, "JOHN-Name" where "JOHN" is the word and "Name" is the entity. NLP is used to analyze the text where these pairs exist and to build rules that classify words into different entities. The resulting NER models are then a set of rules for classifying words into the list of entities. In anonym ization, these entities could be "Patient Name", "Accession Number" and other various PHI identifiers as defined by HIPAA.

There have been two attempts to employ NLP to label and remove PHI in medical reports. Deid PhysioNet is a Perl-based tool that develops models based on an input of PHI lists and then uses these models to identify PHI locations. Deid only works on text files. Deid builds NER models by using NLP on lists of possible PHI words. The lists are of possible patient names, physician names, identifiers, and locations. For example, if the user wishes to deidentify patient names, he/she would have to take a sample of the reports, select the patient names, and store them in a separate list to be fed to Deid. The NER models are built on specific words and not the context of their location. It is impossible to develop a complete list of possible patient names and various other identifiers, such that Deid can reliably deidentify all cases. The probability of over-fitting in these models is also very high, such as where a medical term (e.g., Grave's disease) uses a name. It is also not possible to differentiate between different types of PHI like numerical identifiers and human names that will have the same structure but be in different locations. Deid only works by painstakingly identifying all PHI types and possible values. The user is then left with the odious task of using Deid's findings and anonymizing the reports. It becomes particularly difficult if the user wants to replace PHI with surrogate customized data. In addition, to guarantee that all PHI has been removed, the user reviews each report, which in turn does not cut down the effort or complexity in removing PHI from reports.

MITRE Identification Scrubber Toolkit (MIST) is a Python-based tool that develops models based on annotated free text reports. The user first annotates reports using its in-built annotation tool. This means selecting words and annotating them as either patient name or patient ID or any user-defined tag. These annotated reports are then fed into MIST's model-building to develop NER models that are specific for this set of annotated reports. The location and context of PHI words are taken into account. MIST also provides a mechanism to anonym ize the identified PHI locations. MIST allows the user to build customized models depending on input report structures. MIST only works on free text. MIST, despite its graphical user-interface and in-built annotation tools, is very complex even for seasoned programmers to use. The entire process of annotating, building models and then using models on new data may be very difficult to grasp for its intended users, i.e., radiologist or technicians in hospitals. The complex steps make the entire anonym ization process a not-so-attractive option for hospitals. MIST models cannot be re-used easily. If a user creates a model using MIST on one computer and wishes to give it to another user to anonym ize reports, the second user must download the entire MIST software. It is also not easy to re-use an earlier model to anonym ize the reports must be loaded into MIST.

Even with MIST and Deid available, hospitals still use manual methods to anonym ize their reports (e.g. blanking outpatient names and other PHI fields). Anonym ization of reports is still regarded as a complex problem and finding a practical, easy-enough solution for the hospital sites and their staff to employ is still not solved.

SUMMARY

By way of introduction, the preferred embodiments described below include methods, systems, instructions, and computer readable media for identifying keywords in medical patient data, such as for anonym ization or cohort identification. A conditional random field sequence classifier is used for the NER model for NLP, providing a technical solution to help the computer perform better at identifying PHI from context. One tool or executable integrates report format conversion, annotation, training, and application. These operations may be selected, or the tool configured for anonymization or other keyword identification. Different files from each stage may be exported or used by others operating on other computers, allowing collaboration or sequential burden sharing for anonymization.

In a first aspect, a method is provided for anonymizing medical patient data with a machine-learned system. The medical patient reports for multiple patients of a medical institution are input to a machine-learned condition random field sequence classifier. The medical patient reports include protected health information for the multiple patients. The machine-learned condition random field sequence classifier outputs, in response to the input, anonymized patient data free of the protected health information. The anonymized patient data is then transmitted to an entity other than the medical institution.

In one embodiment, the classifier labels and removes the protected health information. The machine-learned condition random field sequence may have been trained as a linear chain condition random field sequence classifier. The classifier may have been trained on other reports of the same medical institution, providing an NER model trained for the reports of that institution. The classifier is trained as an NER using NLP.

In another embodiment, the medical patient reports are converted from heterogenous formats to a common format. The medical patient reports are input to the classifier in the common format. The converting, inputting, and outputting may be part of a single executable with a library of multiple functions.

In further embodiments, strings (e.g., alphanumeric text strings) are removed from the medical patient reports with a search function prior to the input to the input to the classifier. The strings themselves are a search term or occurring in relation to a search term.

For a re-training embodiment, the machine-learned condition random field sequence classifier may output the medical patient reports with annotations identifying the identified protected health information. The machine-learned condition random field sequence classifier is re-trained based on the medical patient reports with the annotations (e.g., using corrected annotations for re-training).

Using the single executable configured to generate files at different stages, the input and output using the classifier may be performed on one computer while another uses a different instantiation of the same classifier on another computer. In addition to this parallel operation, different parts of the workflow or sequence may be performed by different processors or computers by modular transfer of the files between the computers, such as instantiating multiple processing nodes. For example, the classifier is operated at a cloud server. The output is provided to a computer of the medical institution different than the cloud sever for packaging or review, allowing for a modular and scalable approach.

In some embodiments, multiple classifiers are used. For example, the medical reports are input to the machine-learned condition random field sequence classifier and another machine-learned classifier. The output is an aggregation from the machine-learned condition random field sequence classifier and the other machine-learned classifier. The other machine-learned classifier may be used for part of the anonymization, such as inputting medical images (e.g., DICOM file) and outputting anonymized images (e.g., anonymized DICOM files).

In one embodiment, the inputting and outputting are performed as part of a single executable. The machine-learned condition random field sequence classifier is machine trained as part of the single executable. The same executable may be used to machine train for other purposes, such as machine training another classifier to extract diagnostic or prognostic information as part of the single executable.

In a second aspect, a method is provided for machine-training to anonymize medical patient data. An anonymization tool, including annotation, training, and application of the machine-trained model, is executed. A plurality of first medical reports is annotated, where the annotating identifies patient identifiers in the first medical reports as the annotation. The machine-trained model is machine learned to anonymize the first medical reports from the annotation as the training. The machine-trained model is applied to second medical reports as the application, where the application provides the second medical reports with the patient identifiers removed.

In one embodiment, the executed anonymization tool includes format conversion. The first medical reports in heterogenous formats are converted into a common format as the format conversion. The first medical reports are annotated in the common format.

To support parallel and/or sequential modularity, one embodiment generated different files for different parts of the anonymization process. The first medical reports prior to annotating are in one or more first files. The first medical reports after annotating are in one or more second files. The machine-trained model is in a third file. The second reports with the patient identifiers removed are in one or more fourth files. The annotating, machine learning, and applying may be performed at different computers based on exporting of the one or more first files, the one or more second files, the third file, and/or the one or more fourth files and based on executing the anonymization tool on the different computers.

The executable file may be used for other purposes. The executed anonymization tool may be used to annotate third medical reports for identifications of prognosis or diagnosis and machine training another machine-trained model to determine the prognosis or diagnosis from the identifications. In another embodiment, the anonymization tool "anonymization pipeline" is configured to look for key clinical words. Clinical cohort information may be automatically extracted, and/or population outcome may be mined. Classifiers critical to a cohort may be found for clinical cohort extraction and learning. Other applications using automated mining include population studies, cohort identification, correlation of multiple clinical cohort information across population (e.g. age & gender, age & ethnicity, blood values & ethnicity & outcome), and automated clinical meta data extraction In other embodiments, the machine learning includes training the machine-trained model as a condition random field sequence classifier. As another embodiment, the executed anonymization tool is executed to include user defined rules. The user enters text strings to remove and/or defining locations to be removed as the user defined rules.

In a third aspect, a system is provided for keyword identification of medical reports for export. A medical records database has stored therein a plurality of patient files in different formats. An interface is configured by a machine training anonymization application to receive file identifiers for the plurality of patient files. A processor is configured to convert the plurality of patient files in the different formats into a common format and to machine learn keyword identification based on the patient files in the common format.

The present invention is defined by the following claims, and nothing in this section should be taken as a limitation on those claims. Any embodiments or aspects in one type of claim (e.g., method, system, or non-transitory computer readable media) may be provided in another type of claim. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views. The PHI in the drawings is made up for illustration purposes and does not represent an actual patient.

FIGS. 5A and 5B show example medical reports with PHI identified by user-defined rules;

FIGS. 10A and 10B show example anonymized medical reports;

DETAILED DESCRIPTION OF THE DRAWINGS AND PRESENTLY PREFERRED EMBODIMENTS

Figure 1:
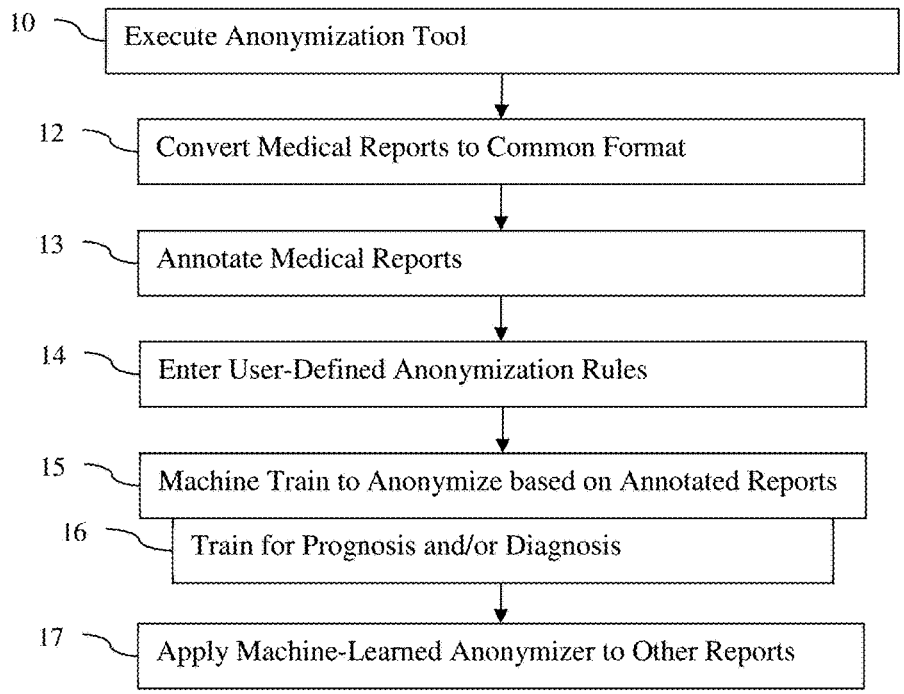
FIG. 1 is a flow chart diagram of an embodiment of a method for machine-training to anonymize medical patient data.

For training artificial intelligence (e.g., machine learning research) in healthcare, large amounts of structured and annotate patient data are needed. Data acquisition from a multitude of sources, including hospitals or other medical institutions, requires anonym ization that complies with local and federal privacy laws (e.g., HIPAA-HITECH in USA and GDPR in EU). PHI should be removed from clinical or other medical reports. To avoid manual labor to anonymize, to reduce data acquisition times, to collect a broader range of information by ease of processing, to allow medical institutions to design their own anonymization, and/or to validate anonym ization, a tool for anonym ization is provided. The tool allows data sources to identify and anonym ize PHI in their reports in a quick, easy and stream-lined manner. The tool's workflow allows it to deal with heterogenous formats and heterogenous structures. The tool may reduce manual labor from the client side, increase flow of more valuable information to designers of artificial intelligence in healthcare, improve collaboration opportunities, reduce data acquisition times, and/or reduce business and legal risks.

The tool machine trains to anonymize medical reports for a given medical institution. The tool operates in a way that makes the computer anonym ize more completely and/or rapidly. The tool may be restructured to annotate and/or extract clinical information.

The same tool may be used to not only anonym ize reports but also to mine relevant clinical metadata from reports or other sets of documents. Users may train the model with appropriate metadata tags, and the trained model finds similar metadata information in other medical reports. Due to the modular operation of the single tool, the final step of replacing the text with surrogate text is not used in the mining. Metadata may include information like presence of specific diagnosis markers, clinical outcome, clinical cohort information, patient body details, and/or previous medical statements. Identifying metadata is useful to classify many reports by the information in their content and/or to develop decision-making tools based on the extracted metadata.

The clinical report anonymization tool employs natural language processing (NLP) and user-defined rules to identify and replace PHI in clinical reports. The tool allows for flexibility with heterogenous structures and heterogenous formats, while reducing the complexity of usage for medical practitioners or administrators, whom lack substantial knowledge in machine training but have access to the medical reports. The tool is based on Python, Perl, or another programming language and packaged in the form of an executable that is easy to install and run.

The tool allows the user to annotate and create NER models for anonymizing. Unlike MIST, the tool uses a suite of functions (e.g., python libraries) to deal with a plethora of different document formats. The reports may be pdfs or any of the MSOffice extensions. This increases the flexibility of the tool, reducing workload for the user who would have otherwise needed to extract text from each report manually.

The tool removes complexities and focuses on the core tasks of annotation and anonymization. By relying on report identification, anonymization, user replacement rule definition, machine training, and application, the overall workflow is straight-forward and understandable, making the entire anonymization process easy to use. Each step of the tool may be performed individually and in different machines. Each step is divided into transportable modules and/or output files that can be run and/or used by different users by using the scripts for that specific module in the tool. This makes the process of anonymization more distributed and less prone to errors. Any mishaps during the workflow may be easily traced. Moreover, modular development allows the tool to be integrated with other external tools, such as DICOM anonymization tools. NER models trained by the tool are stored as files (e.g., tar.gz) that may be given to other users operating different machines. The other users may then directly anonymize their reports using the transferred model and running the anonymization module. This distributed nature of the tool is particularly useful within a medical setup wherein different people perform different functions and access to PHI is limited to different user groups.

In the examples herein, anonymization is performed. The same tool may instead be used for mining clinical information or other purposes where information is removed and/or identified in medical information. For example, keywords may be identified as part of clinical cohort or population heath studies.

Example file extensions are provided in the Figures and description herein. Other file extensions and/or formats may be used, such as a zip or other bundled file extension for a collection of files.

FIG. 1 shows one embodiment of a method for machine training to anonymize medical patient data. A tool with a modular design allows for different machines to perform different acts based on transfer of files. The acts provide for individual, simple approaches to training and application of machine learning, allowing healthcare employees to operate the tool. The machine training is directed to the reports of a given medical institution so that more complete anonymization is provided.

Figure 12:
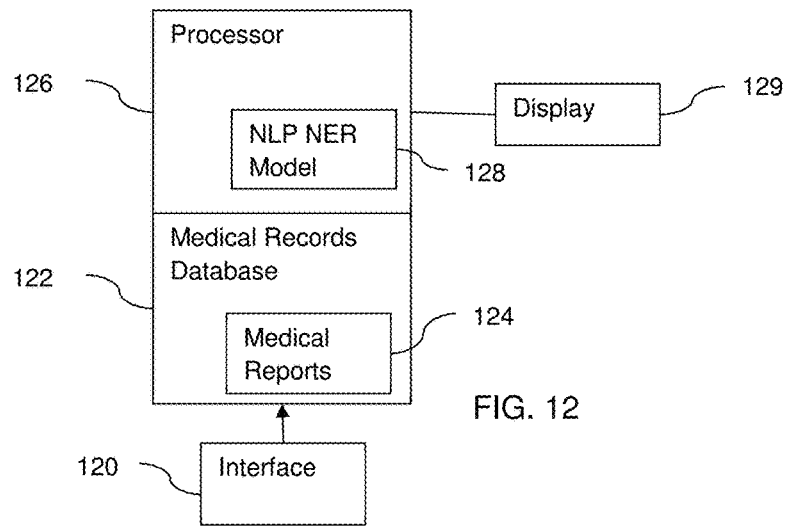
FIG. 12 is a block diagram of one embodiment of a system for anonym ization of medical reports for export.

The method is implemented by the system of FIG. 12 or another system. For example, the method is implemented by a computer, server, or other processor. In another example, the method is implemented by different instances of the same executable file on different computers (e.g., workstations and/or servers). Reports are identified from a medical records database or databases and converted to a common format by one computer running the tool. The same or different computer running the same tool implements the annotation for training of medical reports. The same or different computer running the same tool provides for user definition of anonym ization rules (e.g., identifying to text strings for searching). The same or different computer running the same tool performs the machine training. The same or different computer running the same tool applies the machine-learned NER model.

Additional, different, or fewer acts may be provided. For example, any of acts 12-17 are not performed where one computer is implementing just one or other subset of acts 12-17 and a different computer implements the other acts. As another example, act 14 and/or 16 are not performed. In yet another example, acts for transmitting files between different computers for parallel and/or sequential performance of the acts are included. In this example, the execution of act 10 is repeated for each of the computers.

The acts are performed in the order shown (e.g., top to bottom or numerical) or other orders. For example, act 13 may be performed prior to act 12 where the annotation is provided in various formats. Act 16 may be performed prior to act 15.

In act 10, a processor executes an anonymization application or tool. The tool is provided as an executable file. Rather than downloading and using a collection of different executables or processes, a single executable is provided. The executable is programmed in Python, Perl, C, C++, or other programming language to control the graphics user interface and perform the acts. In other embodiments, different acts are provided by different executable files. Alternatively, one executable file loads different programs for different ones of the acts.

A given instantiation of the executable includes modules for performing the different acts. The executed anonym ization tool includes format conversion, annotation, user-definition of anonym ization rules, training, and/or application of the machine-trained model. A common graphics user interface is provided for selecting and/or performing the different acts or functions. Given this standardization in the graphic user interface and modules, files generated by executing on one computer may be used by executing on another computer.

To avoid complexity and many varied and technical steps, the single executable allows use by the less-technical users from the medical field. Since these less technical users have access to the patient information to be anonym ized, the tool and ease of use make it more likely that anonym ized patient data may be created. The tool focuses on the core tasks of annotation and anonym ization. The overall workflow is straight-forward and understandable, therein making the entire anonym ization process easy to use.

For training an NER model to anonym ize, training data is created. The training data includes sample patient information, such as medical reports (e.g., clinical reports, nursing reports, radiology reports, physician notes, etc.). The user browses one or more sources (e.g., patient medical record databases) to select sample files. Any number of sample medical reports may be selected. The selection is across various sources and/or authors or may be one source and/or one author. The graphics user interface of the tool prompts navigation and selection of sample medical reports to be used for annotation.

In act 12, the processor converts the selected medical reports in heterogenous formats into a common format. Rather than requiring free text or other specific format and thus requiring executing different programs to reformat, the executed tool includes file conversion of different formats used by medical records. The user first selects a sample of the original reports for training. These selected or trainee reports are converted to raw text files by the tool's data import mechanism. The act of selection causes format conversion without further input by the user. Alternatively, the user activates the format conversion and/or selects the formats from or to which to convert. The user has to just provide the path of the folder where these selected sample reports will reside, and the tool converts them to individual text files.

In one embodiment, the executed tool supports adobe portable data format (PDF), MSOffice Formats (ppt, pptx, doc, docx, xls, xlsx), and raw text formats (txt, json, csv). Additional, different, or fewer formats may be supported. The conversion is from any of these supported formats to a given one of the raw text formats, such as txt. Scanned documents, such as handwritten notes or reports, may be converted to text, such as using OCR.

Figure 2:
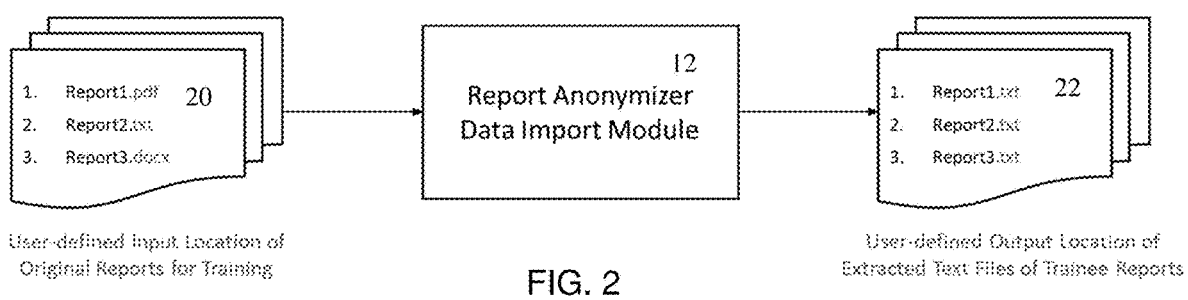
FIG. 2 shows an example method of format conversion of medical reports for anonymization.

The medical reports in any of the supported formats are converted to a common format, such as txt. FIG. 2 shows an example. In one embodiment, the tool uses a suite of python libraries for reading text from different document formats. The medical reports 20 in the different formats are converted 12 as part of data import into medical reports 22 of a same format. Depending on the format of the input file, the tool selects the required library, extracts the text and stores in a separate text file 22 with the same name as input file. The user may provide a location for the output folder for extracted files 22 in the common format. The common format may be other than a free text format. The file conversion as part of the same tool increases the flexibility of the tool greatly and also reduces workload for the user, whom would have otherwise needed to extract text from each report manually.

These extracted text files 22 are sample or trainee medical reports to be annotated by the user to manually setup the training data for the NER model. The rest of the tool uses these extracted text files or text files derived therefrom to run.

Given the file structure represented in FIG. 2, the location of the input files may be distributed as long as the files point to the report anonym ization tool. The output location may also be different locations. The files and operations do not have to run on one work station.

In act 13, the processor provides for annotating the samples of medical reports. The executed tool, using the graphics user interface, prompts the user to sequence through the selected samples and annotate. The user reads the medical reports and identifies any PHI in the medical reports using the graphics user interface. Any patient identifiers are identified by the user and input as an annotation. The PHI is labeled as PHI. For example, annotation is by identifying PHI and tagging each PHI word with a respective entity tag (e.g., "John" identified and tagged as "Name"). Alternatively, PHI is identified without tagging as a specific entity.

The user annotates each selected trainee report. The tool presents the medical reports in the common format. For example, the sample medical reports as text files are annotated. Alternatively, each sample report is presented in its original format.

Figure 3:
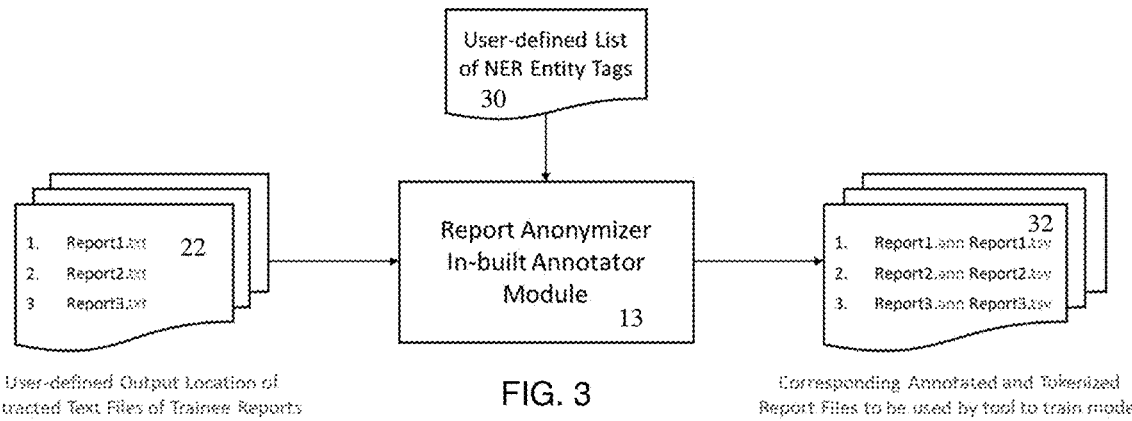
FIG. 3 shows an example method of annotation of medical reports for learning to anonym ize.

FIG. 3 shows one embodiment of annotation. A configuration text file 30 is provided where the user defines what entity tags are required. For example, each type of PHI, based on regulations and/or medical institution standards, is defined, imported as a file, and/or selected from a list. For ease of annotation, corresponding keyboard shortcuts are defined or are linked to the types. For example, in FIG. 4, the entity tags are DATE, PERSON and TIME. Their corresponding shortcuts 40 are o, p and t. Any shortcut key labels may be used. These shortcuts 40 are used to annotate each relevant word with its corresponding tag. Each text file is opened. The user reads the text file, highlights or selects PHI, and tags the PHI using the shortcut 40 as the annotation 13. The keyboard shortcut 40 is used to attach the tag.

Once the shortcuts 40 are defined, the in-built annotator interface is used to annotate each trainee report. The user opens the annotator interface that is part of the tool and selects one of the extracted report text files 22 for annotation. This opens the file in the text area 42. The user then selects a word and presses the desired keyboard shortcut to tag with the corresponding entity tag. All tagged words are highlighted. Other in-built shortcuts in the annotator interface may allow undo, delete, replace tags, next sample, previous sample, and/or other functions.

Figure 4:
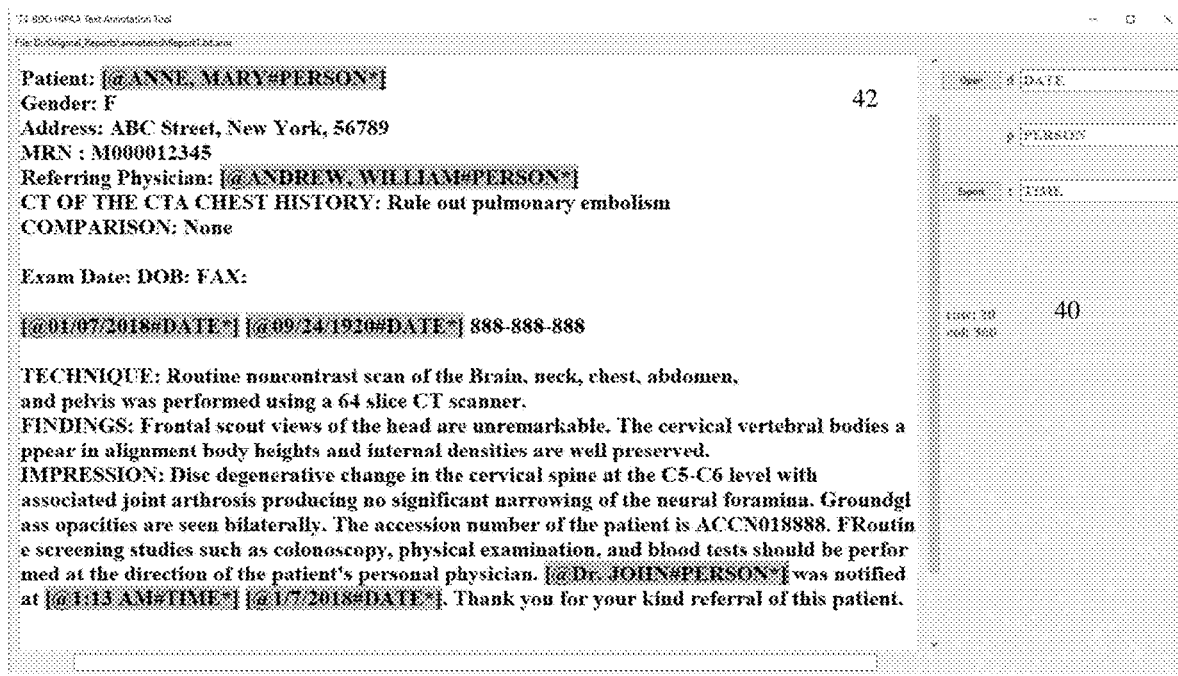
FIG. 4 shows an example annotation.

FIG. 4 is an example of annotation in progress. The user has selected patient names and tagged them with the "PERSON" tag and similarly for dates and times. Once the annotation has been done, the user selects "Export" or "Next Sample," which saves the annotated text file 32 in a separate folder. The user may reopen this annotated text file 32 using the same interface and make changes.

The in-built annotation of the tool also generates and saves a tokenized tab-separated file. The tokenized tab-separated file is a table of all the words in the text file 32 and their corresponding tags. The words include both selected (i.e., identified PHI) and non-PHI words. These tokenized files are used by the tool to create the NER model. Annotated text files 32 end with extension '.ann' or other extension, and tokenized text files end with '.tsv' or other extension.

The user repeats this annotation for all the trainee report text files 22. In other embodiments, the user identifies other information in addition to or instead of the PHI. For example, the user identifies any diagnosis or prognosis. In other examples, the user identifies particular test results, sequence of medical actions, symptoms, and/or other medical information. This non-PHI tagging may be used to machine train extraction of the non-PHI information from medical reports instead of or in addition to anonymization. The tool may be used for either or both.

In act 14 of FIG. 1, the processor, executing the tool, provides for user definition of none, one, or more anonymization rules. The medical institution may use known terminology and/or structure, so the user may define rules to anonymize based on a search or search and replace rule-set. Rather than only relying on the machine learning to identify PHI, manual programming by user entry may identify some PHI. The tool includes a graphics user interface to guide user definition of one or more rules.

In one embodiment, the user enters text strings to remove and/or to define locations to be removed as the user defined rules. The rule may be based on structure so that information at a given locations is identified or identified and removed. The rule may be based on terminology (e.g., alphanumeric text) so that information associated with the terminology is identified or identified and removed. The rule may be based on a combination of terminology and structure. One or more human-identifiable rules are defined.

Apart from patterns found by the machine-trained NLP-NER model, there are also human-identifiable patterns that are constant across some or all of the medical reports. For example, the human-identifiable patterns include header fields and certain texts that appear in header, body, and/or footer locations that could be removed. The tool thus provides an option for the user to define these patterns.

For example, the user defines removable text strings. The text strings that may be outright removed and are constant across the structure of the hospital's reports are identified. The text strings may be location specific (e.g., headers and footers with the hospital's addresses, telephone numbers and also IDs with a specific pattern) or may be located anywhere in the report. FIGS. 5A and 5B show two reports 50, 52 from one hospital. Both reports 50, 52 have the same header and same fax number since they are from one source. Moreover, there is also the accession number of the patient in the Technique body. This value is an alphanumeric word with the initial string "ACC01". Hence, the user can define a removables configuration file to remove particular text strings in anonymization, such as removing: "XYZ Hospital," "ABC Street," "Phone: 333-333-3333," "Fax: 888-888-888," "888-888-888," and "*ACCO*18888." For the accession number or other text strings, the user may just give one example and then enclose the recurring pattern between asterisks. Filler or variable designations may be used for the text string (e.g., "8888" where 8 represents any number, letter, or number and letter").

As another example, headerfields are used to identify information associated with the headerfield. Headerfields are fields, such as in the initial part of the report 50, 52, that have certain form fields filled in while writing the report. The text string identifies the headerfield, and the rule provides for identifying the input text associated with the headerfield as the PHI. From the two reports 50, 52 in FIGS. 5A and 5B, the PHI headerfields are "MRN" and "Address." "Patient" and "Referring Physician" may also be added to the list of headerfields but may instead be accounted for with other rules. The headerfield configuration file may include the text strings of the headerfield, such as "Address:" and "MRN:." The user-defined rule looks for these fields in the reports and then identifies the words at a location (e.g., after) relative to or linked to the text string as PHI.

The rules may be used to (1) identify or (2) identify and delete or replace. For example, the removable text strings are identified and replaced with "REMOVED" in the anonymization process. As another example, the PHI associated with the headerfield text string is replaced with "HEADERFIELD." Other replacement words, redacting (e.g., black block), or mere deletion may be used in anonymization.

Figures 6, 7:
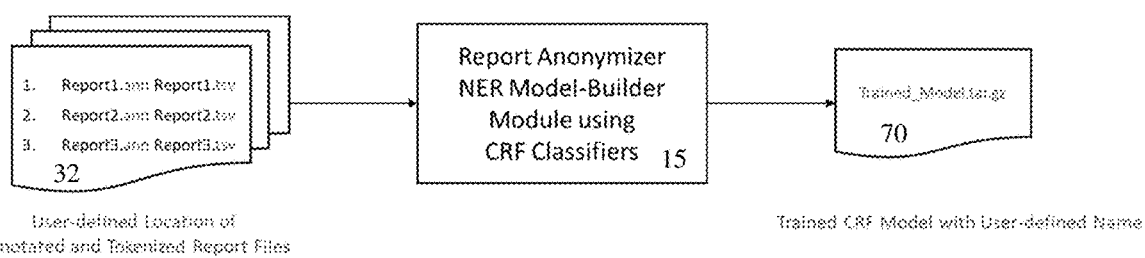
FIG. 6 shows an example of configuration files for user-defined rules.
FIG. 7 shows an example method for machine training an NER model.

FIG. 6 shows two example configuration files resulting from the user definition of rules for the reports of FIGS. 5A and 5B. In other embodiments, additional, different or fewer configuration files defining the rules are provided. In yet other embodiments, additional, different, or fewer rules of one or both of the configuration files are provided.

In act 15 of FIG. 1, the processor performs machine learning. The annotated files are used as training data where the annotations are ground truth and the text files 22 are training samples. The processor performs machine learning to create a machine-trained model to anonymize the medical reports. The machine training is included as part of the same tool (e.g., single executable) used to convert formats and annotate.

Where the anonymization is to identify PHI, then the annotations are used as the ground truth. Where the anonymization is to remove or replace the PHI, then the anonymization files 32 have the identified PHI replaced or removed for training. Alternatively, the machine training is to identify and then rules are used to delete or replace the machine-learned model identified PHI.

In one embodiment, the annotated and tokenized files 32 from the annotation are used by the tool to create the Named Entity Recognition (NER) model using Natural Language Processing (NLP) mechanisms. The NER for NLP may use any of various types of machine learning and corresponding classifiers to identify the PHI in other or unseen reports. In one embodiment, any sequence classifier or classifier that identifies based on textual context in NLP may be used. For example, a condition random field (CRF) sequence classifier is used. As another example, a linear chain CRF Sequence classifier is used as the NER model. The NER model is a CRF classifier. Discrete classifiers predict entity tags without considering the context or neighboring words. CRF classifiers take context into account. Linear Chain CRFs predict sequences of tags using the sequence of words in the context. This is particularly useful for anonymization since PHI in medical data is very much dependent on the context of its location. For example, the word "Gleason" in "Gleason Score" would be classified as potential PHI or human name by normal classifiers, but CRF classifiers would look at the context and understand that it is a name for a particular medical measurement rather than PHI. Words that are not PHI are not removed in the final report, making the anonymized patient data more useful or better for training other artificial intelligence for healthcare. The CRF allows the computer to machine learn better in the medical report context.

FIG. 7 shows an example of machine learning the NER model. The tool automatically selects the files 32. Alternatively, the user provides the location of annotated and tokenized files 32. The user is prompted to input a name and location for the NER model once trained. The in-built model-building script then analyzes the annotated files 32 and creates 15 the model using CRF or other classifiers. The NER model is then saved as an archived '.gz' or other extension file 70. The resulting machine-learned NER model is a CRF classifier for application to anonymize other or unseen reports from the same medical institution.

For training, the training data includes many samples. The samples are the annotation files 32. The samples include medical report text input information and corresponding ground truth or output PHI, removal, or replacement to be learned. The ground truth is the PHI, tag, replacement text, or deletion. The learning based on CRF or other machine learning classifier learns to provide the ground truth from input text.

One NER model is trained to identify multiple entities. Alternatively, different NER models are trained to identify different entities (e.g., one model for Name entity and another model for Date entity). The models may be applied in parallel or sequence to identify the PHI of the various entities.

The trained network is stored in a memory. The trained artificial intelligence (i.e., machine-learned NER model) is stored. The result of the training is a matrix or other model representation.

Any memory may be used. The memory used for the traning data may be used. For application, the memory may be in other devices. For example, the trained model is stored in a memory of a server. The server uses the trained model to output to clients. As another example, multiple copies of the trained model are provided to different users and/or workstations for use by different users.

The tool may be used for other purposes than anonymization. Using CRF or other machine learning, another classifier may be trained in act 16 of FIG. 1 as an NER model in NLP. The other classifier may be to extract diagnostic, prognostic, symptoms, tests, and/or other healthcare information. The single executable, which includes the machine training, uses training data from annotation for the desired output to machine train a classifier or other machine-trained model. The model is trained to determine the prognosis, diagnosis, or other information from unseen reports.

In one embodiment, the machine learns to extract relevant metadata from reports. Metadata may include information like presence of specific diagnosis markers, patient body details, and/or previous medical statements. The heterogenous nature of this tool allows any kind of documents to be annotated and used as training data. Moreover, the user may define what entities have to be annotated and identified through annotation. To extract a specific set of metadata, the user defines the tags, trains the model, and uses the model to annotate new documents. The model then highlights those words that are related to the metadata. The machine-learned classifier is trained to classify any number of reports by the information in their content. The machine-learned classifier may be used to develop decision-making tools that are built from the metadata extracted from reports.

In act 17, the processor applies the machine-trained model to medical reports. For the application part of the executable tool, other reports of the medical institution are applied to anonymize those reports. These other reports are previously unseen by the machine-trained model (i.e., different reports than used to train). The user selects the files 22 for the reports. The reports are converted to a common format and input to the machine-learned NER model. The NER model outputs anonymized reports or PHI labeled reports that may be anonymized using the PHI tags. The machine-learned model provides the reports with the patient identifiers removed or labeled.

Once trained, the machine-learnt network is applied by a machine, such as a computer, processor, or server. The machine uses input data for a patient (e.g., radiology report) and the machine-learned NER model to generate an output, such as an anonymized version of the report.

Figure 8:
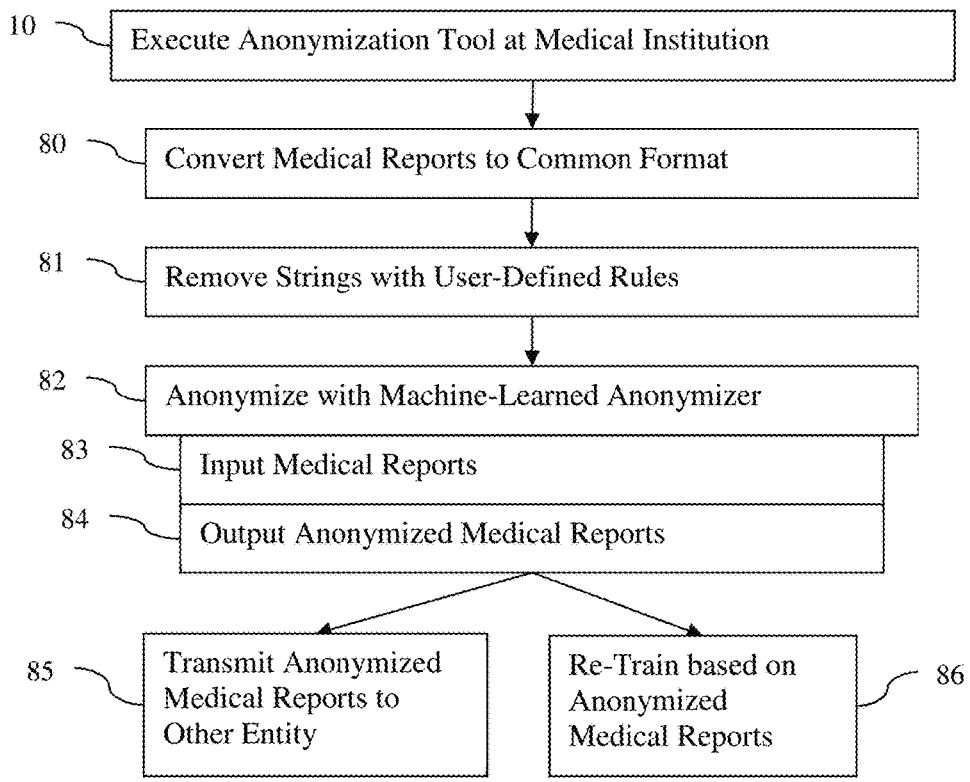
FIG. 8 is a flow chart diagram of an embodiment of a method for anonymizing medical patient data with a machine-learned system.

FIG. 8 shows one embodiment of a method for anonymizing medical patient data with a machine-learned system. The same executable, whether in a same instantiation or a later instantiation and whether by a same processor or a different processor, provides for anonymizing medical patient data. The converting and anonymization (e.g., inputting and outputting of the NER model) are part of a single executable with a library of multiple functions. The application of the machine-learned model (i.e., inputting medical reports and outputting anonymized reports) is performed as part of the single executable.

Additional, different, or fewer acts may be provided. For example, act 81 is not performed. As another example, either or both of acts 85 and 86 are not performed. In yet other examples, acts for transmitting files between computers are provided.

The acts are performed in the order shown (e.g., top to bottom or numerical) or other orders. For example, acts 81 and 82 are performed in a reverse order.

The method is implemented by the system of FIG. 12 or another system. For example, the method is implemented by a computer, server, or other processor. For example, one computer is used to convert, and another computer is used to remove text strings and apply the NER model.

In act 10, the anonymization tool is executed. The processor loads and runs the tool. The execution may be a continuation from the training on the same computer or may be a re-instantiation (i.e., executing the tool again) on the same or different computer.

The application may be performed by a same or different processor used for training. For example, the NER model file 70 is transmitted to a different computer, such as where one person creates the NER model and one or more other people are to apply the model to reports of one or more databases at the medical institution. The NER model (e.g., machine-learned CRF sequence classifier) is implemented by the executed tool on the other computer to anonymize reports of the medical institution. Since the training was specific to reports of the medical institution, the learned system may better anonymize other reports of that same medical institution.

In one embodiment, the annotating, machine learning, and applying are at different computers based on exporting of the one or more files 20, 22, 32, 60, 70, and/or anonymized reports from any of the modules or functions of the tool. The anonymization tool is executed in different instantiations on the different computers but can operate on any of the files on any of the computers. Each step of the tool may be performed individually and in different machines. Each step is divided into transportable modules that may be run by different users by only using scripts of that specific module. This makes the process of anonymization more distributed and less prone to errors. Any mishaps during the workflow may be easily traced. Moreover, modular development allows integration with other external tools. The NER model trained by the tool is stored as tar.gz or other extension file, which may be given to other users using different machines. The other users may then directly anonymize their reports using this transported NER model and only running the anonymization module of the executed tool. This distributed nature of the tool is particularly useful within a medical setup wherein different people perform different functions and access to PHI is limited to different user groups.

Figure 9:
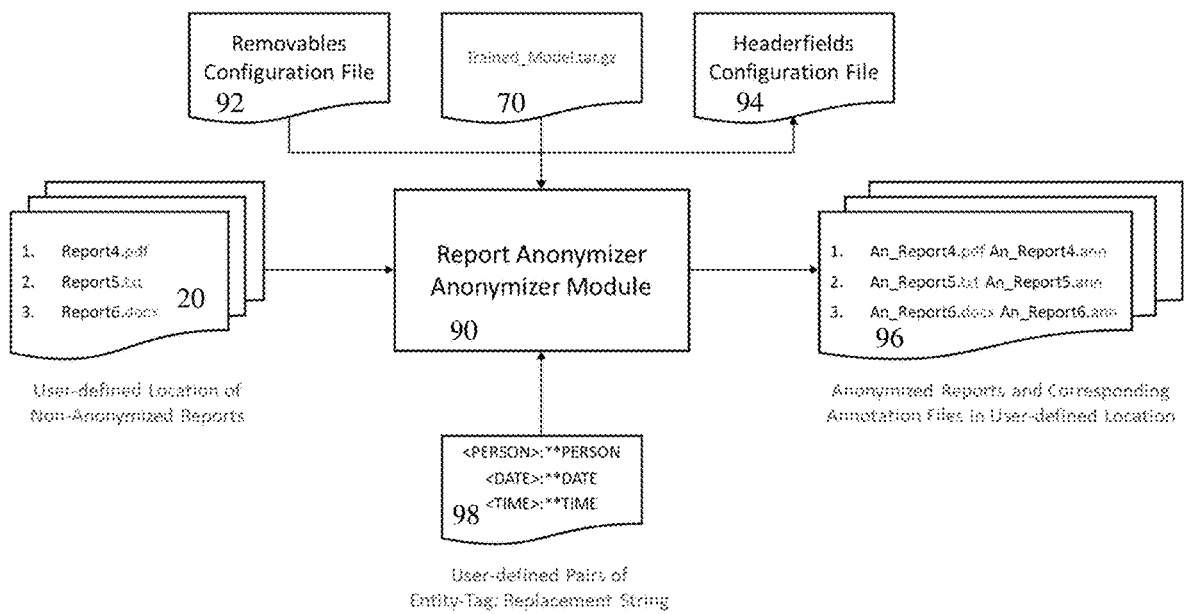
FIG. 9 shows an example method of anonymizing medical reports.

FIG. 9 shows one embodiment. The in-built anonymizer script 90 is an anonymizing module or function of the tool. The user uses the trained NER model 70 and user-defined rules (e.g., removables and headerfield configuration files 92, 94) to anonymize new reports 20. The location of new reports 20 along with which trained model and configuration files 92, 94 to be used are input or selected by the user. The selected reports 20 are input to the script 90 to anonymize, creating the anonymized reports 96 with or without annotation files indicating the changes. The output reports 96 are stored in a user-defined or default location.

In act 80 of FIG. 8, the report or reports 20 with medical patient information are converted, where not in the common format, to the common format. The new reports 20 may be in any of the supported formats. Any reports in the heterogeneous formats are converted by the script 90 to the common format, such as a text format. The same conversion used for annotating may be used. The conversion is automatic upon selection of the medical report or reports to be anonymized. Alternatively, the user selects and then separately triggers conversion.

In act 81, the processor applies the user-defined rules. Alternatively, new rules are defined after training and in preparation for anonymizing with the NER model.

Individual rules are selected and applied. In other embodiments, the rule configuration files are called by the tool and applied as a group of rules. In one embodiment, the rules include removable text strings and the corresponding removable configuration file 92 and include headerfield text strings and the corresponding headerfield configuration file 94.

The report or reports are searched for the defined text strings. The PHI as defined by the text strings is identified through the search. Each report is searched to identify each instance of each text string. For removables, the text string itself is the PHI. The PHI is the search term. For headerfields, the text linked to the text string is the PHI. The PHI occurs in relation to the search term.

The identified PHI is removed. The removal may merely delete the PHI from the report. In other embodiments, the PHI is removed by replacement. A user-defined or default table or file 98 of the entity tag and replacement string is used to replace. For example, any identified name is tagged by the rule as a person entity. This person information is replaced by "**PERSON."

The user-defined rules are applied before applying the NER model to reduce the processing burden of the NER model and/or reduce the number of mistakes in anonymization. In alternative embodiments, the NER model is applied in act 82 prior to applying the user-defined rules in act 81.

The reports 22 with the anonymization provided by the user-defined rules are input in act 83 to the NER model to anonymize in act 82. The machine-learned anonymizer anonymizes the input reports 22 using the script 90. To gather samples for artificial intelligence training, a large number of reports are input for anonymization. Various reports for various patients of a medical institution are selected and input for anonymization. The reports 22 being input are in the common format. In alternative embodiments, the NER model is trained to receive reports in various supported formats.

In one embodiment, the NER model is operated by a server. The user computer transmits the reports 22 for input to the NER model by the server, such as a cloud server controlled by the medical institution or a partner with arranged access to the patient medical data.

The NER model is a condition random field sequence or other classifier for identifying and/or replacing (e.g., by deletion or substitution) PHI in the input reports. The NER model was trained using NLP by the previously performed training to identify and/or replace PHI in the reports. Since the prior training was on similar reports of the same medical institution, the NER model may more accurately identify and replace PHI. In alternative embodiments, the NER model is trained on reports from one institution and applied to reports at a different institution.

In one embodiment, the NER model using NLP was trained as a deep machine-learnt network. For NLP, the deep-machine-learned network may be a recursive neural network and/or a long term-short memory network. Any architecture may be used. Other deep learnt, sparse auto-encoding models may be trained and applied. Other natural language processing tools may also be included. Computational linguistics (e.g., linguist rules), information retrieval, and/or knowledge representation may be part of the natural language processing system.

Upon activation, the in-built anonym izer script 90 extracts text from each report 22, using the NER model or models to annotate the text. The NER model or models may only identify or may identify and replace. In one embodiment, the NER model identifies and then a rule is applied to replace the identified PHI with an appropriate replacement string from the replacement configuration file 98. The annotated words with their respective entity tags are replaced.

Other machine-learned classifiers may be applied. For example, the reports include medical images in the report or linked to the report. A machine-learned model, such as for anonymizing DICOM files, is applied to the images so that the images are anonymized.

In act 84, the NER model outputs the anonymized reports. The annotated and anonymized files 96 are saved in either text or converted back to a same format as original report 20. The annotations of new reports generated by the model (i.e., reports with PHI identified but not removed) may be stored separately so as to facilitate review.

The machine-learned CRF sequence classifier outputs in response to the input of the reports. The output is of anonym ized patient data free of the PHI, such as free of patient identifying information. The PHI may be labeled (i.e., PHI identified or annotated) and/or removed by the CRF sequence classifier. In other embodiments, personal identifiable information (PII), such as credit card numbers, phone numbers, or social security numbers, are removed or labeled.

The output is to memory, a computer network, server, or another computer. In one embodiment, the computer or cloud server implementing the script 90 outputs to a different computer of the medical institution for verification or review.

Where more than one machine-learned classifier is applied, the output is aggregated from both. For example, anonymized images output by one classifier replace images in the report, and text anonymized by another classifier replaces text in the report. Where different NER classifiers are used for different types of entities, the labels and/or replacements from each are aggregated to form one anonym ized report.

FIGS. 10A and 10B show two example anonymized reports 100, 102. The anonymization is provided by user-defined rules applied in act 81 and anonymization performed in act 82. Since CRF is used, medical terms based on proper names are more likely to remain. Since CRF is used, unusual PHI is more likely to be removed based on the use of context. The computer operates in a way that improves the output results.

In act 85, he output is transmitted to an entity other than the medical institution. The personal at the medical institution anonymize before transmission to avoid violation of regulations. The tool is used to anonymize efficiently and provides for more accurate anonymization by the computer. After any verification, the anonym ized medical reports are sent to another entity, such as a team training artificial intelligence to operate based on the medical data or to use the medical data for research. Due to the efficient anonym ization, medical institutions are more likely to transmit the medical reports over a computer network to another entity.

In act 86, the anonym ized reports are used for re-training the machine-learned CRF sequence classifier. The output reports with the labels may be reviewed. Any inaccuracies or corrections are noted. The output reports are updated to remove and/or add PHI labels inaccurately provided or not provided by the CRF classifier. These corrections and/or the corrected annotations may be used to re-train or train again the classifier.

In one embodiment, the annotation files output by the classifier are saved by the tool. These annotation files may be opened using the in-built annotation interface. In case the user is not satisfied with anonymization results, the user corrects their corresponding annotation files. The corrected annotation files are then used as trainee reports. The machine learning is performed again with the training data including the additional trainee reports to build the NER model again. Consequently, the NER model may more completely anonym ize once re-trained. Re-training allows for improvement of the NER model as more and more heterogenous reports are used in training, thereby expanding the corpus of correctly annotated reports.

Figure 11:
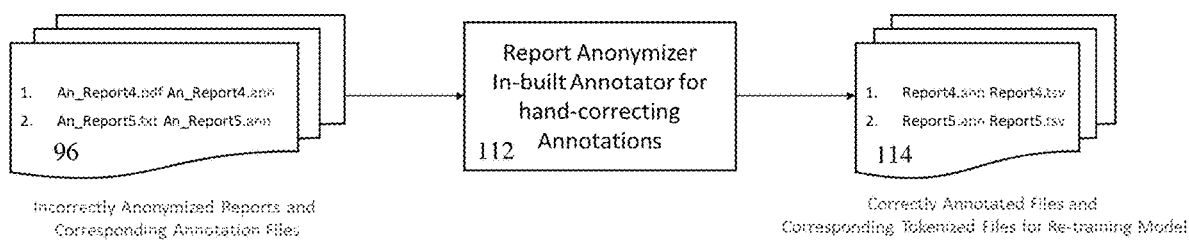
FIG. 11 shows an example use of anonymized medical reports for re-training an NER model.

FIG. 11 shows an example. The annotated reports 96 are reviewed. Any reports 110 with inaccuracies are identified and hand corrected 112. The result are additional correctly annotated files and corresponding tokenized files 114 to be used in training.

The tool may generate a CSV or other file of all PHI words found during the anonym ization process for each report. This allows the user to quickly verify the results instead of opening each file.

The pipeline or tool is easily configurable. For example, one, a subset, or all of annotation, user-defined rules, removal of user-defined strings, tokenizing header with key or value pairs, providing user defined strings, or other modules may be selected and added to pipeline for a given use. For retraining, the pipeline as configured or reconfigured by the selection is applied, such as using the acts of FIG. 1 where the acts used are based on the selection. The anonymization strategy fine tuned until to get needed results by adding layers of components to take care of any PHI issues. In the clinical curation use cases, components are added to identify specific clinical keywords as needed.

FIG. 12 shows a block diagram of one embodiment of a system for anonymization of medical reports for export. The system is for training and/or application of the machine-learned model. An executable file is used to provide file conversion, annotation, rule definition, machine training, and application of the machine-learned CRF model.

The system implements the method of FIGS. 1, 2, 3, 7-9 and/or 11 and/or other natural language processing to ano-nym ize and/or train a NLP to anonym ize. Other methods or acts may be implemented, such as acts for selecting the radiology report, designating storage locations, transmitting files, and/or using the answer.

The system includes an interface 120, one or more medical records databases 122 with one or more radiology reports 124, a processor 126 for applying a natural language processing via the NER model 128, and a display 129. Additional, different, or fewer components may be provided. For example, a network or network connection is provided, such as for networking with a medical imaging network or data archival system or interconnecting the processor 126 and the database 122. In another example, additional processors 126, databases 122, and/or NER models 128 are provided.

The interface 120, medical records database 122, processor 126, and/or display 129 are part of a medical imager, server, workstation, or computer. In one embodiment, the interface 120, medical records database 122, processor 126, and/or display 129 are a personal computer, such as desktop or laptop. In yet other embodiments, the medical records database 122 is part of a separate computer from the processor 126.

The interface 120 is a user interface, such as user input device (e.g., keyboard, mouse, trackpad, touchscreen, and/or roller ball). The interface 120 may be a bus, chip, or other hardware for receiving user input interacting with an anonym ization tool. The display 129 may be part of the graphical user interface 120.

The interface 120 is configured by a machine training anonymization application to receive file identifiers for the plurality of patient files (e.g., medical reports 124). Other information may be received and/or output, such as annotations, rule definitions, file conversion, folder designation, shortcut definition, other inputs, outputs, or user interactions with any of the modules or functions of the anonymization application or tool. The configuration is provided by software, hardware, and/or firmware. For example, the interface 120 is configured by an operating system to receive user entry of selection of the reports 124 and annotation of the reports 124.

The medical records database 122 is a random access memory, system memory, cache memory, hard drive, optical media, magnetic media, flash drive, buffer, database, combinations thereof, or other now known or later developed memory device for storing the radiology reports 124, the NER model 128, and/or data generated by natural language processing (e.g., files, configuration files, entities, labels, anonym ized reports, rules, and/or replacement text). The medical records database 122 is part of the computer associated with the processor 126 or is a separate or remote database for access over a computer network. More than one database 122 may be provided, such as separate databases for different practice groups and/or locations in a same medical institution. The database or databases 122 store a plurality of patient files (e.g., patient medical records including one or more medical reports for each patient). The patient files may be stored in one or more formats.

The medical records database 122 or other memory is alternatively or additionally a non-transitory computer readable storage medium storing data representing instructions executable by the programmed processor 126. The instructions for implementing the anonymization tool or application are stored. The instructions for implementing the processes, methods, and/or techniques discussed herein are provided on non-transitory computer-readable storage media or memories, such as a cache, buffer, RAM, removable media, hard drive, or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The processor 126 is a general processor, control processor, digital signal processor, application specific integrated circuit, field programmable gate array, or other hardware processor for natural language processing. The processor 126 is part of a computer, workstation, server, or other device configured to apply machine learning and/or to apply a machine-learned model 128. The processor 126 is configured by software, hardware, and/or firmware. For learning, the processor 126 is configured by one or more machine learning algorithms. For applying a learned model 128, the processor 126 is configured, in part, by a learned matrix or matrices, table, or other model representation associating input data to output data.

The processor 126 is configured to receive user selection of patient files, to convert the plurality of patient files in the different formats into a common format, to prompt and receive user annotation, to prompt and receive user-defined rules, to machine learn anonym ization based on the patient files in the common format, and to apply the machine-learned NER model. One executable includes programming for the various functions. The format of files communicated between functions allows for different instantiations of the application or tool on different computers to perform the different functions collaboratively. The processor 126 may be configured for re-training and/or transmission of anonymized patient files.

The display 129 is a monitor, LCD, projector, plasma display, CRT, printer, or other now known or later developed device for displaying a file browser, graphics user interface of the tool or application, reports, labels, entities, rules, replacement text, or other information used by the tool or application. The processor 126 formats the data into an image and stores the image in a buffer, configuring the display 129. The display 129 uses the image in the buffer to generate an image for viewing. The image includes graphics, alphanumeric text, anatomical scan, and/or other information, such as text for the anonym ized reports.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for anonymizing medical patient data with a machine-learned system, the method comprising:

acquiring medical patient reports in different formats for multiple patients of a medical institution, the different formats including at least portable data formats, MSOffice Formats, and raw text formats;

converting the medical patient reports to a common format;

inputting the converted medical patient reports to a machine-learned condition random field sequence classifier trained to predict sequences of tags using a context of a sequence of words, the medical patient reports including protected health information for the multiple patients;

extracting and analyzing text from the converted medical patient reports by the machine-learned condition random field sequence classifier;

annotating, replacing, or annotating and replacing at least a portion of the text in the converted medical patient reports by the machine-learned condition random field sequence classifier based on the analysis;

outputting, by the machine-learned condition random field sequence classifier in response to the inputting, anonymized patient data free of the protected health information; and transmitting the anonymized patient data to an entity other than the medical institution.

2. The method of claim 1 wherein outputting comprises labeling and removing the protected health information by the machine-learned condition random field sequence having been trained as a linear chain condition random field sequence classifier.

3. The method of claim 1 wherein the converting, inputting, and outputting are part of a single executable with a library of multiple functions.

4. The method of claim 1 wherein the machine-learned condition random field sequence classifier was trained on other reports of the medical institution.

5. The method of claim 1 wherein inputting comprises inputting to the machine-learned condition random field sequence classifier as a named entity recognition model using natural language processing.

6. The method of claim 1 further comprising removing strings from the medical patient report with a search function prior to the inputting, the strings being a search term or occurring in relation to a search term.

7. The method of claim 1 further comprising:
outputting, by the machine-learned condition random field sequence classifier, the medical patient reports with annotations identifying the protected health information; and re-training the machine-learned condition random field sequence classifier based on the medical patient reports with the annotations.

8. The method of claim 1 wherein inputting and outputting are performed on a first computer, and further comprising operating the machine-learned condition random field sequence classifier on a second computer different than the first computer.

9. The method of claim 1 wherein inputting comprises inputting to the machine-learned condition random field sequence classifier at a cloud server and wherein outputting comprises outputting to a computer of the medical institution different than the cloud server.

10. The method of claim 1 wherein inputting comprises inputting to the machine-learned condition random field sequence classifier and another machine-learned classifier, and wherein outputting comprises outputting an aggregation from the machine-learned condition random field sequence classifier and the other machine-learned classifier.

11. The method of claim 10 wherein inputting to the other machine-learned classifier comprises inputting medical images and wherein outputting by the other machine-learned classifier comprises outputting anonymized images.

12. The method of claim 1 wherein inputting and outputting are performed as part of a single executable, and further comprising:
machine training the machine-learned condition random field sequence classifier as part of the single executable; and
machine training another classifier to extract diagnostic or prognostic information as part of the single executable.

13. A method for machine-training to anonymize medical patient data, the method comprising:

executing an anonymization tool, the executed anonymization tool including annotation, training, and application of the machine-trained model;

acquiring first medical reports in different formats, the different formats including at least portable data formats, MSOffice Formats, and raw text formats;

converting the first medical reports to a common format;

annotating the converted first medical reports, the annotating identifying patient identifiers in the first medical reports as the annotation;

machine learning the machine-trained model to predict sequences of tags using a context of a sequence of words to anonymize the converted first medical reports from the annotation as the training; and applying the machine-trained model to second medical reports to extract and analyze text from the second medical reports and then annotate, replace, or annotate and replace at least a portion of the text, the application providing the second medical reports with the patient identifiers removed.

14. The method of claim 13 wherein the first medical reports prior to annotating are in one or more first files, wherein the first medical reports after annotating are in one or more second files, wherein the machine-trained model is in a third file, and wherein the second reports with the patient identifiers removed are in one or more fourth files, and further comprising performing the annotating, machine learning, and applying at different computers based on exporting of the one or more first files, the one or more second files, the third file, and/or the one or more fourth files and based on instantiations of the anonymization tool on the different computers.

15. The method of claim 13 further comprising, with the executed anonymization tool, annotating third medical reports for identifications of prognosis or diagnosis, and machine training another machine-trained model to determine the prognosis or diagnosis from the identifications.

16. The method of claim 13 wherein machine learning comprises training the machine-trained model as a condition random field sequence classifier.

17. The method of claim 13 wherein executing comprises executing with the executed anonymization tool including user defined rules, and further comprising entering, by the user, text strings to remove and/or defining locations to be removed as the user defined rules.

18. A system for keyword identification of medical reports for export, the system comprising:
a medical records database having stored therein a plurality of patient files in different formats, the different formats including at least portable data formats, MSOffice Formats, and raw text formats;

an interface configured by a machine training anonymization application to receive file identifiers for the plurality of patient files; and a processor configured to convert the plurality of patient files in the different formats into a common format and to machine learn keyword identification based on the patient files in the common format by predicting sequences of tags using a context of a sequence of words, the processor further configured with the machine training anonymization application to extract and analyze text from the plurality of patient files and then annotate, replace, or annotate and replace at least a portion of the text providing the plurality of patient files with the patient identifiers removed.

* * * * *